| United States Patent [19] | [11] 4,087,419 |
|---|---|
| Tinney | [45] May 2, 1978 |

[54] HEPTAPEPTIDES AND METHODS FOR THEIR PRODUCTION

[75] Inventor: Francis John Tinney, Ann Arbor, Mich.

[73] Assignee: Parke, Davis & Company, Detroit, Mich.

[21] Appl. No.: 739,164

[22] Filed: Nov. 5, 1976

[51] Int. Cl.$^2$ .................... C07C 103/52; A61K 37/00
[52] U.S. Cl. .................. 260/112.5 LH; 260/112.5 R; 424/177
[58] Field of Search ............... 260/112.5 R, 112.5 LH

[56] References Cited

U.S. PATENT DOCUMENTS

| 3,247,180 | 4/1966 | Schwyer et al. | 260/112.5 R |
| 3,247,182 | 4/1966 | Schwyer et al. | 260/112.5 R |
| 3,256,526 | 6/1966 | Schwyer et al. | 260/112.5 R |
| 3,787,386 | 1/1974 | Flouret et al. | 260/112.5 LH |

OTHER PUBLICATIONS

R. Schwyer et al., Helv. Chim. Acta, No. 95, 1963, pp. 870–889.

J. Ramachandran et al., J. Am. Chem. Soc. 87, 1965, pp. 2691–2695.

*Primary Examiner*—Delbert R. Phillips
*Attorney, Agent, or Firm*—Stephen Raines; Frank S. Chow; David B. Ehrlinger

[57] ABSTRACT

New heptapeptides having the formula X-Ser(benzyl)-Tyr(benzyl)-Phe-Leu-Arg(R)-Pro-Gly-Y wherein X is a protective group, R is a protective group and Y is lower alkoxy, amino, lower alkylamino or di(lower alkyl)amino.

3 Claims, No Drawings

HEPTAPEPTIDES AND METHODS FOR THEIR PRODUCTION

SUMMARY AND DETAILED DESCRIPTION

The present invention relates to new peptide compounds that are useful as luteinizing hormone releasing factor antagonists and to methods for their production. More particularly, the invention relates to new N-protected heptapeptides that are represented by the formula X-Ser(benzyl)-Tyr(benzyl)-Phe-Leu-Arg(R)-Pro-Gly-Y     (I)

wherein X is a protective group, preferably t-butoxycarbonyl or benzyloxycarbonyl, R is a protective group, preferably nitro or (4-methylphenyl)sulfonyl and Y is lower alkoxy, amino, lower alkylamino or di(lower alkyl)amino.

The preferred compounds of formula I are those wherein X is t-butoxycarbonyl or benzyloxycarbonyl, R is nitro or (4-methylphenyl)sulfonyl and Y is methoxy, amino or ethylamino.

In formula I, the conventional symbols for amino acid residues of peptide compounds linked thereto are used and each is intended to have the following meaning: Pro, D-prolyl or L-prolyl; Tyr(benzyl), D-tyrosyl(benzyl) or L-tyrosyl(benzyl); Ser(benzyl), D-seryl(benzyl) or L-seryl(benzyl); Phe, D-phenylalanyl or L-phenylalanyl; Leu, L-leucyl or D-leucyl; Arg, D-arginyl or L-arginyl; and Gly, glycyl. In addition, the term "lower alkyl" is intended to mean a straight, branched or cyclic hydrocarbon moiety of up to six carbon atoms, such as methyl, ethyl, isopropyl and cyclopropyl and "lower alkoxy" is intended to mean an alkoxy group having a straight, branched or cyclic hydrocarbon moiety of up to six carbon atoms, such as methoxy, ethoxy and isopropoxy. A protective group as defined for X is intended to mean a group usually employed in the area of peptides for protecting an amino function, such groups are disclosed in the following texts which are incorporated by reference: E. Schroder and K. Lubke, "The Peptides", Vol. I, Chapter 1., Academic Press, 1966 and J. Meienhofer in "Hormonal Proteins and Peptides", Vol. II, p. 227., Academic Press, 1973. A protective group as defined for R is intended to mean a group usually employed for protecting the $N^G$-guanidino moiety of the amino acid arginine. Such groups are also disclosed in the above cited references. These symbols and terms will also be used in the formulae that follow for other compounds and each such symbol or term should be understood to have the meaning given above.

In accordance with this invention, compounds of the formula I, wherein X and R are as previously defined and Y is lower alkoxy, are produced by removing a protected heptapeptide from a resin complex of the following structure X-Ser(benzyl)-Tyr(benzyl)-Phe-Leu-Arg(R)-Pro-Gly-resin     II wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference; preferably the resin is a crosslinked copolymer comprising 98 to 99 percent polystyrene crosslinked with 1 to 2 percent divinylbenzene, which is attached to the protected heptapeptide through a methyleneoxy bridge wherein the methylene group is attached to the polymeric portion of the resin and the oxygen atom is attached to the protected heptapeptide and X and R are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° C. to about 35° C.

While a large excess of the lower alkyl alcohol is preferred, only a catalytic amount of tertiary amine is required; however, larger amounts are preferred, such as about 10 percent volume/volume based on the amount of lower alkyl alcohol employed.

While it is not a preferred procedure, compounds of the formula I wherein Y is amino, lower alkylamino or di(lower alkyl)amino may be prepared by reacting compounds of the formula II wherein X and R are as previously defined, with ammonia, lower alkylamine or di(-lower alkyl)-amine.

The resin complex is suspended in a solvent, such as methanol, ethanol, dimethylformamide, etc., at a temperature of from about 0° C. to 50° C. for periods of from 12 hours to 10 days. When employing less reactive amines, the preferred solvent is dimethylformamide.

Certain of the complex resins of the formula II are prepared by coupling a protected amino acid of the formula X-Ser(benzyl)-OH     III with complex resins of the formula Tyr(benzyl)-Phe-Leu-Arg(R)-Pro-Gly-resin     IV wherein X and R are as previously defined in formula I, in an organic solvent, such as dichloromethane with the aid of dicyclohexylcarbodiimide. The three reactants may be used in abut equimolar quantities, but excess amounts of the protected amino acid and dicyclohexylcarbodiimide are sometimes advantageous. The reaction is generally conducted at about room temperature for a period of from about fifteen minutes to about 20 hours.

The complex resins of the formula IV are prepared by treating complex resins of the formula t-butoxycarbonyl-Tyr(benzyl)-Phe-Leu-Arg(R)-Pro-Gly-resin     V with a large excess of trifluoroacetic acid utilizing dichloromethane as the solvent at temperatures of from 20° C. to 30° C. for about 10 minutes followed by neutralization of the trifluoroacetic acid salt with a base such as triethylamine.

The complex resins of the formula V are prepared by coupling t-butoxycarbonyl-Tyr(benzyl)-OH to complex resins of the formula Phe-Leu-Arg(R)-Pro-Gly-resin     VI using the reaction procedure described for the preparation of compounds of the formula II.

The complex resins of the formula VI are prepared by treating the complex resins of the formula t-butoxycarbonyl-Phe-Leu-Arg(R)-Pro-Gly-resin    VII with trifluoroacetic acid using the reaction procedure for the preparation of compounds of the formula IV.

The complex resins of the formula VII are prepared by coupling t-butoxycarbonyl-Phe-OH to complex resins of the formula Leu-Arg(R)-Pro-Gly-resin    VIII according to the procedure used for the preparation of compounds of formula II.

The complex resins of the formula VIII are prepared by treating the complex resins of the formula t-butoxycarbonyl-Leu-Arg(R)-Pro-Gly-resin    IX with trifluoroacetic acid using the reaction procedure for the preparation of compounds of the formula IV.

The complex resins of the formula IX and other useful complex resins are prepared by coupling t-butoxycarbonyl-Leu-OH to complex resins of the formula Arg(R)-Pro-Gly-resin    X according to the procedure used for the preparation of compounds of the formula II.

The complex resins of the formula X are prepared by treating the complex resins of the formula t-butoxycarbonyl-Arg(R)-Pro-Gly-resin    XI with trifluoroacetic acid using the reaction procedure for the preparation of compounds of the formula IV.

Certain of the complex resins of formula XI are prepared by coupling t-butoxycarbonyl-Arg(R)-OH to complex resins of the formula Pro-Gly-resin    XII according to the procedure used for the preparation of compounds of formula II.

The complex resins of the formula XII are prepared by treating the complex resins of the formula t-butoxycarbonyl-Pro-Gly-resin    XIII with trifluoroacetic acid using the reaction procedure for the preparation of compounds of formula IV.

Certain of the complex resins of formula XIII are prepared by coupling t-butoxycarbonyl-Pro-OH to a complex resin of the formula Gly-resin according to the procedure used for the preparation of compounds of formula II.

In accordance with this invention, compounds of the formula I, wherein X and R are as previously described and Y is amino, lower alkylamino or di(lower alkyl)amino are prepared by reacting a compound of the formula I wherein Y is alkoxy, preferably methoxy, with ammonia, lower alkylamine or di(lower alkylamine).

The reactions are conducted at temperatures of from about 5° C. to 100° C. for from 3 hours to 4 days, preferably about room temperature. Generally, a large excess of amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

Compounds of the formula I wherein X and R are as described in formula I and Y is amino, lower alkylamino or di(lower alkyl)amino are prepared by coupling a compound of the formula X-Ser(benzyl)-Tyr(benzyl)-Phe-Leu-Arg(R)-Pro-Gly-OH    XIV with ammonia, a lowr alkylamine or a di(lower alkyl)amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° C. to 50° C., preferably room temperature for periods of from 10 hours to 5 days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula XIV are prepared by the hydrolysis of a compound of formula I wherein X and R are as previously defined and Y is lower alkoxy. The reaction is conducted at temperatures of from 20° C. to 30° C. using about 0.5 ml. of two normal aqueous sodium hydroxide solution and 10 ml. of solvent, usually water or an alcohol such as methanol, for each millimole of ester. The compound of formula XIV is isolated after acidification with aqueous citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Heptapeptides of this invention were screened for LRF antagonist activity in vitro using rat anterior pituitary cell cultures as described by Vale et. al. [Endocrinology, 91, 562 (1972)]. The inhibition of LRF (luteinizing hormone releasing factor) induced luteinizing hormone (LH) release into the culture medium is the endpoint in this in vitro bioassay.

Following are the results of the above tests on certain preferred compounds.

ACTIVITY TABLE FOR IN VITRO TEST IN RAT ANTERIOR PITUITARY CELL CULTURES

| | Molar Conc. | LH Value ng/ml. | % LH Release Inhibition |
|---|---|---|---|
| $N^\alpha$-t-Butoxycarbonyl-O-benzyl-L-seryl-O-benzyl-L-tyrosyl-D phenylalanyl-L-leucyl-$N^G$-nitro-L-arginyl-L-prolyl-glycine methyl ester | $1 \times 10^{-7}$ | 13.94 | 90 |
| LRF Control | $5 \times 10^{-10}$ | 25.36 | |
| Saline Control | | 12.62 | |
| $N^\alpha$-t-Butoxycarbonyl-O-benzyl-L-seryl-O-benzyl-L-tyrosyl-D-phenylalanyl-L-leucyl-$N^G$-tosyl-L-arginyl-L-prolyl-glycine methyl ester | $1 \times 10^{-7}$ | 23.79 | 74 |
| LRF Control | $5 \times 10^{-10}$ | 56.01 | |
| Saline Control | | 12.17 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH-RH, and its biological activity, see Science, Vol. 174, No. 4008, Oct. 29, 1971, pages 511–512. Thus, the heptapeptides of this invention are useful in controlling ovulation and in restricting fertility.

The invention is illustrated by the following examples.

EXAMPLE 1

$N^\alpha$-t-Butoxycarbonyl-O-benzyl-L-seryl-O-benzyl-L-tyrosyl-D-phenylalanyl-L-leucyl-$N^G$-[(4-methylphenyl)sulfonyl]-L-arginyl-L-prolyl-glycine methyl ester $N^\alpha$-t-Butoxycarbonyl-O-benzyl-L-seryl-O-benzyl-L-tyrosyl-D-phenylalanyl-L-leucyl-$N^G$-[(4-methylphenyl)sulfonyl]-L-arginyl-L-prolyl-glycine resin, 3 g., is suspended in a mixture of 20 ml. of triethylamine and 200 ml. of methanol. The suspension is stirred at room temperature for three days, filtered and the solvents evaporated to give 0.81 g. of the above named product as a hemihydrate after chromatography over silica gel using methanol:benzene (20:80); m.p. 100°–105° C.

$N^\alpha$-t-Butoxycarbonyl-O-benzyl-L-seryl-O-benzyl-L-tyrosyl-D-phenylalanyl-L-leucyl-$N^G$-[(4-methylphenyl)sulfonyl]-L-arginyl-L-prolyl-glycine resin is obtained from 20 g. of $N^\alpha$-t-butoxycarbonyl glycine resin by successive couplings, according to the General Procedure given below, of 1) 4.1 g. (0.019 mol) of $N^\alpha$-t-butoxycarbonyl-L-proline and 3.9 g. (0.019 mol) of dicyclohexylcarbodiimide 2) 8.5 g. (0.019 mol) of $N^\alpha$-t-butoxycarbonyl-$N^G$-[(4-methylphenyl)sulfonyl]-L-arginine and 3.9 g. (0.019 mol) of dicyclohexylcarbodiimide, 3) 4.4 g. (0.019 mol) of $N^\alpha$-t-butoxycarbonyl-L-leucine and 3.9 g. (0.019 mol) of dicyclohexylcarbodiimide, 4) 5.0 g. (0.019 mol) of $N^\alpha$-t-butoxycarbonyl-D-phenylalanine and 3.9 g. (0.019 mol) of dicyclohexylcarbodiimide, 5) 7.05 g. (0.019 mol) of $N^\alpha$-t-butoxycarbonyl-O-benzyl-L-tyrosine and 3.9 g. (0.019 mol) of dicyclohexylcarbodiimide and 6) 5.6 g. (0.019 mol) of $N^\alpha$-t-butoxycarbonyl-O-benzyl-L-serine and 3.9 g. (0.019 mol) of dicyclohexylcarbodiimide.

$N^\alpha$-t-Butoxycarbonyl glycine resin is obtained by refluxing 100 g. (0.116 mol) of 1% chloromethylated resin, 22.3 g. (0.13 mol), of $N^\alpha$-t-butoxycarbonyl glycine and 12.9 g. (0.13 mol) of triethylamine in 500 ml. of ethanol for four days. Nitrogen analysis shows 0.00063 mol per gram.

General Procedure for the Solid Phase Synthesis of Peptide Resins

The peptide resin is obtained by attaching an α-amino-protected amino acid to a resin (usually a chloromethylated resin which is commercially available from Lab systems, Inc., San Mateo, Calif.). The peptide system is then constructed by de-protecting the α-amino-protected amino acid resin and attaching an α-amino-protected amino acid. Repetition of this process produces the peptide resin having the required number and sequence of the desired peptide. The terminal α-amino protection is changed by de-protection and attaching the desired carboxylic terminal group. The solid phase synthesis procedure is described by J. M. Stewart "Solid Phase Peptide Synthesis," W. H. Freeman and Co., 1969.

Each cycle of the procedure follows the scheme:
1. De-protection with excess 50% trifluoroacetic acid in dichloromethane.
2. Three washes with dichloromethane.
3. Neutralization of the trifluoroacetic acid salt with an excess of cold 10% triethylamine in dichloromethane.
4. Three washes with dichloromethane.
5. Fifteen to thirty minutes agitation with the α-amino-protected amino acid which is present in up to a fourfold molar excess based on the resin nitrogen analysis. However when a large excess of the α-amino-protected amino acid is used it is agitated with the resin for 15 minutes and the excess recovered by draining the solution from the reactor.
6. Addition of dicyclohexylcarbodiimide at least equivalent to the α-amino-protected amino acid in Step 5 in dichloromethane followed by agitation for four to twenty hours. In the alternate method, a 3.3-fold excess of dicyclohexylcarbodiimide is used relative to the α-amino-protected amino acid resin.
7. Three washes with dichloromethane.

EXAMPLE 2

N$^\alpha$-t-Butoxycarbonyl-O-benzyl-L-seryl-O-benzyl-L-tyrosyl-D-phenylalanyl-L-leucyl-N$^G$-nitro-L-arginyl-L-prolyl-glycine methyl ester N$^\alpha$-t-Butoxycarbonyl-O-benzyl-L-seryl-O-benzyl-L-tyrosyl-D-phenylalanyl-L-leucyl-N$^G$-nitro-L-arginyl-L-prolyl-glycine resin, 0.75 g., is suspended in a mixture of 50 ml. of methanol and 5 ml. of triethylamine. The suspension is stirred at room temperature for two days, filtered and the solvents evaporated to give 0.2 g. of product, containing 2.5 moles of water, after chromatography over silica gel using methanol: benzene (10:90); m.p. 105°–110° C.

N$^\alpha$-t-Butoxycarbonyl-O-benzyl-L-seryl-O-benzyl-L-tyrosyl-D-phenylalanyl-L-leucyl-N$^G$-nitro-L-arginyl-L-prolyl-glycine resin is obtained from 12 g. of N$^\alpha$-t-butoxycarbonyl glycine resin by successive couplings of 1) 2.14 g. (0.01 mol) of N$^\alpha$-t-butoxycarbonyl-L-proline and 2.1 g. (0.01 mol) of dicyclohexylcarbodiimide, 2) 3.1 g. (0.01 mol) of N$^\alpha$-t-butoxycarbonyl-N$^G$-nitro-L-arginine and 2.1 g. (0.01 mol) of dicyclohexylcarbodiimide, 3) 2.3 g. (0.01 mol) of N$^\alpha$-t-butoxycarbonyl-L-leucine and 2.1 g. (0.01 mol) of dicyclohexylcarbodiimide, 4) 2.7 g. (0.01 mol) of N$^\alpha$-t-butoxycarbonyl-D-phenylalanine and 2.1 g (1.01 mol) of dicyclohexylcarbodiimide, 5) 3.7 g. (0.01 mol) of N$^\alpha$-t-butoxylcarbonyl-O-benzyl-L-tyrosine and 2.1 g. (0.01 mol) of dicyclohexylcarbodiimide and 6) 2.95 g. (0.01 mol) of N$^\alpha$-t-butoxycarbonyl-O-benzyl-L-serine and 2.1 g. (0.01 mol) of dicyclohexylcarbodiimide.

N$^\alpha$-t-Butoxycarbonyl glycine resin is obtained by refluxing 100 g. (0.116 mol) of 1% chloromethylated resin, 25 g. (0.14 mol) of N$^\alpha$-t-butoxycarbonyl glycine and 13 g . (0.13 mol) of triethylamine in 400 ml. of ethanol for two days. Nitrogen analysis shows 0.00083 mol per gram.

I claim:

1. A heptapeptide of the formula t-butoxy-L-Ser(benzyl)-L-Tyr(benzyl)-D-Phe-L-Leu-L-Arg(R)-L-Pro-Gly-lower alkoxy where R is nitro or (4-methylphenyl)sulfonyl.

2. The heptapeptide of claim 1 having the name N$^\alpha$-t-butoxycarbonyl-O-benzyl-L-seryl-O-benzyl-L-tyrosyl-D-phenylalanyl-L-leucyl-N$^G$-[(4-methylphenyl)sulfonyl]-L-arginyl-L-prolyl-glycine methyl ester.

3. The heptapeptide of claim 1 having the name N$^\alpha$-t-Butoxycarbonyl-O-benzyl-L-seryl-O-benzyl-L-tyrosyl-D-phenylalanyl-L-leucyl-N$^G$-nitro-L-arginyl-L-prolyl-glycine methyl ester.

* * * * *